United States Patent
Azulay et al.

(10) Patent No.: US 11,931,113 B2
(45) Date of Patent: Mar. 19, 2024

(54) SYSTEMS, DEVICES, AND METHODS FOR RETRACTOR INTERFERENCE AVOIDANCE

(71) Applicant: Mazor Robotics Ltd., Caesarea (IL)

(72) Inventors: Shmuel Azulay, Tel Aviv (IL); Moshe Shoham, Hoshaya (IL)

(73) Assignee: Mazor Robotics Ltd., Caesarea (IL)

( * ) Notice: Subject to any disclaimer, the term of this patent is extended or adjusted under 35 U.S.C. 154(b) by 163 days.

(21) Appl. No.: 17/357,659

(22) Filed: Jun. 24, 2021

(65) Prior Publication Data
US 2022/0031399 A1 Feb. 3, 2022

Related U.S. Application Data

(60) Provisional application No. 63/060,485, filed on Aug. 3, 2020.

(51) Int. Cl.
| | |
|---|---|
| *A61B 17/02* | (2006.01) |
| *A61B 34/20* | (2016.01) |
| *A61B 34/30* | (2016.01) |
| *A61B 90/50* | (2016.01) |
| *A61B 90/00* | (2016.01) |

(52) U.S. Cl.
CPC ............. *A61B 34/20* (2016.02); *A61B 17/02* (2013.01); *A61B 34/30* (2016.02); *A61B 90/50* (2016.02); *A61B 2090/367* (2016.02); *A61B 2090/376* (2016.02); *A61B 2090/3966* (2016.02)

(58) Field of Classification Search
CPC ................ A61B 17/02–0293; A61B 34/20–30
See application file for complete search history.

(56) References Cited

U.S. PATENT DOCUMENTS

| | | | | |
|---|---|---|---|---|
| 7,806,891 B2 * | 10/2010 | Nowlin | .................. | A61B 34/30 606/1 |
| 9,283,047 B2 | 3/2016 | Namiki | | |
| 9,486,133 B2 | 11/2016 | Lee et al. | | |
| 9,532,838 B2 * | 1/2017 | Coste-Maniere | ...... | A61B 34/35 |
| 9,795,367 B1 | 10/2017 | Lee et al. | | |

(Continued)

FOREIGN PATENT DOCUMENTS

| | | |
|---|---|---|
| EP | 3482694 | 5/2019 |
| KR | 10-2012-0007107 | 1/2012 |
| WO | WO 2016/164590 | 10/2016 |

OTHER PUBLICATIONS

International Search Report and Written Opinion for International (PCT) Patent Application No. PCT/IL2021/050929, dated Dec. 6, 2021, 14 pages.

(Continued)

*Primary Examiner* — Eduardo C Robert
*Assistant Examiner* — Steven J Cotroneo
(74) *Attorney, Agent, or Firm* — Sheridan Ross P.C.

(57) ABSTRACT

Systems and methods for retractor interference avoidance is provided. At least one retractor includes a base and one or more elongate members extending from the base. The one or more elongate members are movable. A position of the at least one retractor may be determined and a trajectory of a surgical device may be received. At least one elongate member of the one or more elongate members positioned to interfere with movement of the device along a trajectory may be identified based on the position of the retractor and the trajectory of the surgical device.

10 Claims, 6 Drawing Sheets

(56) References Cited

U.S. PATENT DOCUMENTS

| | | | |
|---|---|---|---|
| 9,872,733 B2 | 1/2018 | Shoham et al. | |
| 9,937,014 B2 | 4/2018 | Bowling et al. | |
| 10,058,338 B2 | 8/2018 | Shoham | |
| 10,299,883 B2 | 5/2019 | Kilroy et al. | |
| 10,463,440 B2 | 11/2019 | Bowling et al. | |
| 10,512,509 B2 | 12/2019 | Bowling et al. | |
| 10,531,926 B2 * | 1/2020 | Roessler | A61B 34/10 |
| 2014/0316436 A1 | 10/2014 | Bar et al. | |
| 2015/0374446 A1 * | 12/2015 | Malackowski | A61B 34/10 606/130 |
| 2018/0199999 A1 * | 7/2018 | Syverson | A61B 90/00 |
| 2018/0271603 A1 | 9/2018 | Nir et al. | |
| 2019/0117310 A1 * | 4/2019 | Hiratsuka | A61B 34/70 |
| 2019/0201104 A1 | 7/2019 | Shelton, IV et al. | |
| 2019/0380794 A1 | 12/2019 | Al Jewad et al. | |
| 2020/0069377 A1 * | 3/2020 | Finley | A61B 90/37 |
| 2020/0146731 A1 * | 5/2020 | Tillett | A61B 34/30 |
| 2022/0110701 A1 * | 4/2022 | Crawford | A61B 90/37 |

OTHER PUBLICATIONS

Atyabi et al. "Review of classical and heuristic-based navigation and path planning approaches," International Journal of Advancements in Computing Technology, Jan. 2013, vol. 5, 14 pages.

Bauzano et al. "Planning Automatic Surgical Tasks for a Robot Assistant," Motion and Operation Planning of Robotic Systems, Mechanisms and Machine Science, Mar. 2015, vol. 29, pp. 193-220.

Bauzano et al. "Auto-Guided Movements on Minimally Invasive Surgery for Surgeon Assistance," IEEE/RSJ International Conference on Intelligent Robots and Systems, Nov. 2018, pp. 1843-1848.

Kim et al. "A development of assistant surgical robot system based on surgical-operation-by-wire and hands-on-throttle-and-stick," BioMedical Engineering OnLine, 2016, vol. 15, Article 58, 19 pages.

KROVI "Robotic Surgery: In Safe Hands," Dynamic Systems & Control, Sep. 2015, vol. 3, No. 3, 24 pages.

Leung et al. "Robotic liver surgery," Hepatobiliary Surgery and Nutrition, 2014, vol. 3, No. 5, pp. 288-294.

Nguyen et al. "End-Effector Path Planning and Collision Avoidance for Robot-Assisted Surgery," International Journal of Precision Engineering and Manufacturing, Dec. 2016, vol. 17, No. 12, pp. 1703-1709.

* cited by examiner

SYSTEMS, DEVICES, AND METHODS FOR RETRACTOR INTERFERENCE AVOIDANCE

CROSS REFERENCE TO RELATED APPLICATIONS

This application claims the benefit of U.S. Provisional Application No. 63/060,485, filed on Aug. 3, 2020, and entitled "Systems, Devices, and Methods for Retractor Interference Avoidance", which application is incorporated herein by reference in its entirety.

FIELD

The present technology is related generally to retractors and the use thereof, and more particularly, to avoiding collisions between retractors and surgical devices.

BACKGROUND

Retractors are used to retract patient tissue at a surgical site to create a clear path for surgical tools to reach the site. Retractors may be positioned and left in place for a portion or the duration of a surgical procedure. A surgical plan may include a trajectory along which a surgical instrument may be inserted into a patient. Surgical robots may be used in some surgeries to assist a surgeon (including, for example, by aligning a surgical instrument along a predetermined trajectory), or in other surgeries to carry out a surgery autonomously.

SUMMARY

Example aspects of the present disclosure include:

A system for retractor interference avoidance according to at least one embodiment of the present disclosure comprises: at least one retractor having a base and one or more elongate members extending from the base, the one or more elongate members being movable; a memory for storing instructions; a processor executing instructions stored in the memory that cause the processor to: determine a position of the at least one retractor; receive a trajectory of a surgical device; identify, based on the position of the retractor and the trajectory of the surgical device, at least one elongate member of the one or more elongate members positioned to interfere with movement of the device along the trajectory.

Any of the aspects herein, wherein executing the instructions stored in the memory further causes the processor to cause the at least one elongate member to move from an initial position and away from the trajectory.

Any of the aspects herein, further comprising at least one motor for moving the at least one elongate member.

Any of the aspects herein, wherein executing the instructions stored in the memory further causes the processor to transmit a notification for notifying a user to manually move the at least one elongate member.

Any of the aspects herein, wherein executing the instructions stored in the memory further causes the processor to receive robot positional data corresponding to a position of a robot, the at least one retractor coupled to the robot.

Any of the aspects herein, wherein determining the position of the at least one retractor is based on the robot positional data.

Any of the aspects herein, wherein executing the instructions stored in the memory further causes the processor to: receive at least one image depicting the at least one retractor, and register the at least one retractor to a patient space, wherein determining the position of the at least one retractor is based on the registration.

Any of the aspects herein, wherein executing the instructions stored in the memory further causes the processor to receive a three-dimensional (3D) model of the at least one retractor, and wherein the registration is further based on the 3D model.

Any of the aspects herein, wherein the at least one retractor includes a fluoroscopic marker detectable by a fluoroscope.

Any of the aspects herein, wherein the executing the instructions stored in the memory further causes the processor to cause the at least one elongate member to return to the initial position.

A method for avoiding retractor interference according to at least one embodiment of the present disclosure comprises: determining a position of at least one retractor, the at least one retractor having a base and one or more elongate members extending from the base, the one or more elongate members being movable; receiving a trajectory of a surgical device; identifying based on the position of the retractor and the trajectory of the surgical device, at least one elongate member of the one or more elongate members positioned to interfere with movement of the device along the trajectory; and causing the at least one elongate member to move from an initial position and away from the trajectory.

Any of the aspects herein, wherein determining the position of the at least one retractor includes determining a position of each elongate member of the one or more elongate members.

Any of the aspects herein, further comprising receiving robot positional data corresponding to a position of a robot, the at least one retractor coupled to the robot.

Any of the aspects herein, wherein determining the position of the at least one retractor is based on the robot positional data.

Any of the aspects herein, further comprising: receiving at least one image depicting the at least one retractor, and registering the at least one retractor to a patient space, wherein determining the position of the at least one retractor is based on the registration.

Any of the aspects herein, further comprising receiving a three-dimensional (3D) model of the at least one retractor, and wherein the registering is further based on the 3D model.

Any of the aspects herein, further comprising transmitting a notification for notifying a user to manually move the at least one elongate member.

A surgical retractor according to at least one embodiment of the present disclosure comprises: a base; a plurality of elongate members extending from the base and configured to engage an anatomy of a patient; and a motor configured to selectively retract at least one elongate member of the plurality of elongate members towards the base upon receipt of a first signal, and to extend the at least one elongate member of the plurality of elongate members from the base upon receipt of a second signal received after the first signal.

Any of the aspects herein, wherein the at least one retractor includes a fluoroscopic marker detectable by a fluoroscope.

Any of the aspects herein, wherein each elongate member of the plurality of elongate members is retractable and extendable independently of any other elongate member of the plurality of elongate members.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
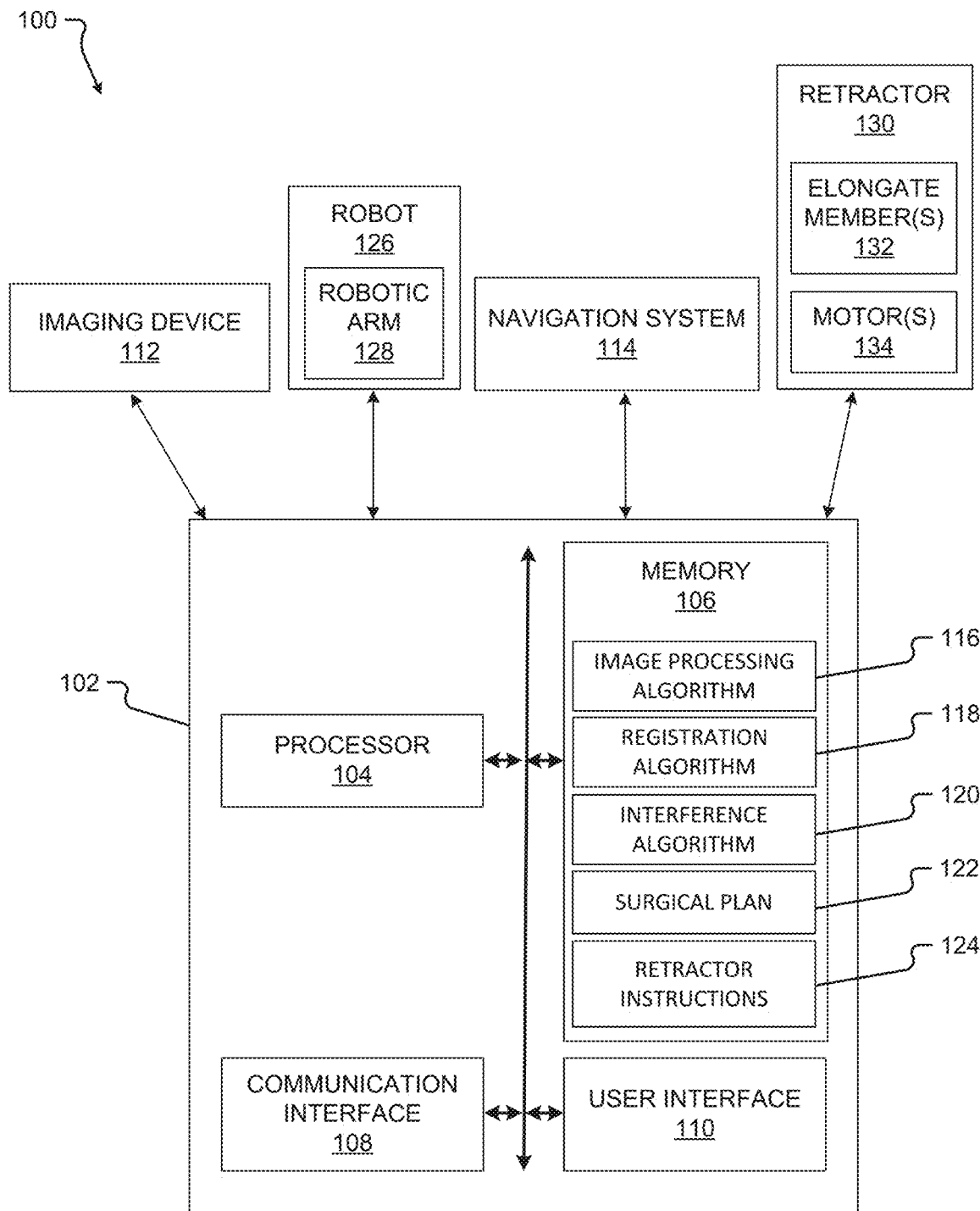
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

Mechanical attachment of a robot guide system to a patient's soft tissue retractors during an open procedure is desirable to decrease patient movement during the robotic procedure as there is a risk of anatomy shift during a robotic procedure. The robotic procedure is based on a registration process followed by the execution process. One of the challenges is restraining the patient's movement due to unstable anesthesia or a surgeon pressure on the patient after the registration process. One way to achieve patient fixation is by connecting the robotic system to designated retractors.

In a small open procedure, the surgeon can apply pressure on the patient that might cause the spine to move, which causes inaccurate execution of the robotic movement planned. In addition to or instead of being mounted to a bone of the patient, a robot may be attached to one or more retractors which might increase the patient restrained procedure, and support a more accurate robotic spine surgery.

In some spine procedures, designated retractors have been designed to support a standardized solution of retraction. This is a 1-2 level spinal fusion surgery using pedicle screws in cortical trajectories. In a robotic procedure, these retractors can be connected to the robot to increase patient fixation.

During a spine surgery, a surgeon may use retractors to retract the soft tissue. From time to time these retractors are in the way of a tool trajectory, for example a drill that is directed to the pedicle. Embodiments of the present disclosure include a system to predict trajectory interference with retractors during operation, which would allow the user to manually or automatically move a retractor part to avoid a collision with a robot or tool moving along a predetermined trajectory without changing the patient anatomic location or the trajectory. A system according to at least one embodiment of the present disclosure allows a registration process via fluoroscopic intraoperative imaging. The system will recognize the location of the retractors and calculate whether a tool on a trajectory is going to hit the retractors. The retractors may be modifiable in one or more ways in order to avoid a collision. In one option, comb-like retractors are utilized, in which each retractor comprises a plurality of extensions or teeth, and each extension or tooth can be disassembled, removed, or otherwise moved. Each extension or tooth may also be marked to facilitate disassembly, removal, or movement of the extension or tooth. One or more sensors may be utilized to assist in determining whether a collision is likely or imminent, and if so, the system may instruct the user which extension or tooth should be disassembled, removed, or otherwise moved. In another option, the retractor comprises one or more mechanisms that enable each extension or tooth thereof to be shifted automatedly. Such retractors may comprise a displacement motor system, that displaces one or more teeth to allow an obstacle-free trajectory. Modification of a retractor to clear a path for a surgical tool or robot as described herein does not change the patient anatomy, so no re-reregistration of the patient anatomy is required.

Embodiments of the present disclosure also provide for a robotic platform for mounting to a surgical retractor used to restrain a patient during surgery. The surgical retractor may be one or more soft-tissue retractors used during a robotic procedure. The retractor(s) can be attached to the robotic platform system to improve patient movement restriction during surgery. During a robotic procedure, and after a registration process, the system assumes the patient is not moving with respect to the robot. This assumption may be compromised with the mobility of the patient, and the forces being applied by the surgeon. Attachment of the robot to a bone of the patient can limit patient movement relative to the robot. Securing the robot to one or more retractors provides an additional level of mechanical fixation of the robot to the patient.

As described more fully below, methods and systems for avoiding retractor interference with a surgical tool using elongate members capable of moving or being moved without removal of the entire retractor may beneficially reduce operating time and provide a streamlined process. The retractor may also be connected to a robot, thereby improving stability and reducing movement of a patient.

Turning first to FIG. 1, a block diagram of a system 100 according to at least one embodiment of the present disclosure is shown. The system 100 may be used to facilitate fixation of a patient relative to a robot (or vice versa), and/or to prevent or avoid a collision between a retractor and a robotic arm or other surgical instrument. The system 100 may additionally or alternatively be used to execute an interference algorithm 120, an image processing algorithm 116, and/or a registration algorithm 118; and/or to carry out other aspects of one or more of the methods disclosed herein. The system 100 comprises a computing device 102, an imaging device 112, a navigation system 114, a robot 126, a retractor 130, and/or a motor 134. The retractor 130 may include one or more elongate members 132 configured to engage an anatomy of a patient. Systems according to other embodiments of the present disclosure may comprise more or fewer components than the system 100. For example, the system 100 may not include the imaging device 112, navigation system 114, the motor 134, and/or the robot 126. Embodiments of the present disclosure may comprise more than one of any of the components of the system 100, including specifically the imaging device 112, the robot 126, the robotic arm 128, the retractor 130, and/or the motor 134.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 126, and/or the navigation system 114.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 500 and/or 600 described herein. The memory 106 may store, for example, one or more image processing algorithms 116, one or more registration algorithms 118, one or more interference algorithms 120, one or more retractor instructions 124, and/or one or more surgical plans 122. Such algorithms and/or instructions may, in some embodiments, be organized into one or more applications, modules, packages, layers, or engines. The algorithms and/or instruction may cause the processor 104 to manipulate data stored in the memory 106 and/or received from the imaging device 112, the robot 126, and/or the navigation system 114.

The computing device 102 may also comprise a communication interface 108. The communication interface 108 may be used for receiving image data or other information from an external source (such as the imaging device 112, the navigation system 114, the robot 126, and in some embodiments the retractor 130), and/or for transmitting instructions, images, or other information to an external system or device (e.g., another computing device 102, the navigation system 114, the imaging device 112, the robot 126, and/or the retractor 130). The communication interface 108 may comprise one or more wired interfaces (e.g., a USB port, an ethernet port, a Firewire port) and/or one or more wireless interfaces (configured, for example, to transmit information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, touchscreen, headset, and/or any other device for receiving information from a user and/or for providing information to a user. The user interface 110 may be used, for example, to receive a user selection or other user input regarding receiving image data depicting at least one retractor; to receive a user selection or other user input regarding registering the at least one retractor to a patient space or other coordinate space; to receive a user selection or other user input regarding determining a position of at least one retractor; to receive a user selection or other user input regarding a trajectory of a surgical device; to receive a user selection or other user input regarding identifying at least one elongate member of one or more elongate members positioned to interfere with movement of the device along the trajectory; to receive a user selection or other user input regarding causing the at least one elongate member to move from an initial position and away from the trajectory; and/or to display image data, the retractor instructions 124, and/or the surgical plan 122. In some embodiments, the user interface 110 may be useful to allow a surgeon or other user to modify the plan 122, or other information displayed, though it will be appreciated that each of the preceding inputs may be generated automatically by the system 100 (e.g., by the processor 104 or another component of the system 100) or received by the system 100 from a source external to the system 100. In some embodiments, user input such as that described above may be optional or not needed for operation of the systems, devices, and methods described herein.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 may be operable to image a patient and/or the retractor 130 to yield an image and image data corresponding to the image. The imaging device 112 may be capable of taking a 2D image or a 3D image to yield the image data. "Image data" as used herein refers to the data generated or captured by an imaging device, including in a machine-readable form, a graphical form, and in any other form. In various examples, the image data may comprise data corresponding to an anatomical feature of the patient or a portion thereof (e.g., a spinal region) and/or the retractor 130 (or a reference marker positioned on the retractor 130). The imaging device 112 may be or comprise a fluoroscope, an ultrasound probe, an O-arm, a C-arm, a G-arm, or any other device utilizing X-ray-based imaging (e.g., a CT scanner, or other X-ray machine), a magnetic resonance imaging (MRI) scanner, an optical computed tomography scanner, an endoscope, a telescope, a thermographic camera (e.g., an infrared camera), or any other imaging device suitable for obtaining images of a patient.

The navigation system 114 may provide navigation for a surgeon and/or a surgical robot during an operation. The navigation system 114 may be any now-known or future-developed navigation system, including, for example, the Medtronic StealthStation™ S8 surgical navigation system. The navigation system 114 may include a camera or other sensor(s) for tracking one or more reference markers, navigated trackers, or other objects within the operating room or other room where a surgical procedure takes place. In various embodiments, the navigation system 114 may be used to track a position of the imaging device 112 (or, more particularly, of a navigated tracker attached, directly or indirectly, in fixed relation to the imaging device 112), of the retractor 130 (or, more particularly, of a navigated tracker attached, directly or indirectly, in fixed relation to the retractor 130), and/or of the robot 126 (or, more particularly, of a navigated tracker attached, directly or indirectly, in fixed relation to the robot 126). The navigation system 114 may include a display for displaying one or more images from an external source (e.g., the computing device 102, imaging device 112, or other source) or a video stream from the camera or other sensor of the navigation system 114. In some embodiments, the system 100 can operate without the use of navigation system 114.

The robot 126 may be any surgical robot or surgical robotic system. The robot 126 may be or comprise, for example, the Mazor X™ Stealth Edition robotic guidance system. The robot 126 may comprise a robotic arm 128. In some embodiments, the robotic arm 128 may comprise a plurality of robotic arms. For example, the robot 126 may comprise two robotic arms or more than two robotic arms. In some examples, the robotic arm 128 may hold one or more retractors 130.

Reference markers (i.e., navigation markers) may be placed on the robot 126, the robotic arm 128, the imaging device 112, the retractor 130 or any other object in the surgical space. The reference markers may be tracked by the navigation system 114, and the results of the tracking may be used by the robot 126 and/or by an operator of the system 100 or any component thereof. In some embodiments, the navigation system 114 can be used to track other components of the system 100 (e.g., imaging device 112 and/or retractor 130) and the system 100 can operate without the use of the robot 126 (e.g., with the surgeon manually manipulating the imaging device 112 and/or the retractor 130).

The motor 134 is operable to move elongate members 132 of the retractor 130. In some embodiments, the retractor 130 includes one motor 134 or more than one motor 134. In other embodiments, the retractor 130 may not include a motor and the elongate members 132 may be manually moved or removed from the retractor 130 by a surgeon or other operator. The motor 134 may be an electric motor with a rotor and stator, a linear induction motor, a pneumatic motor, a hydraulic motor, a gear motor, an AC brushless motor, a DC brushed motor, a DC brushless motor, a servo motor, or the like.

Figure 2:
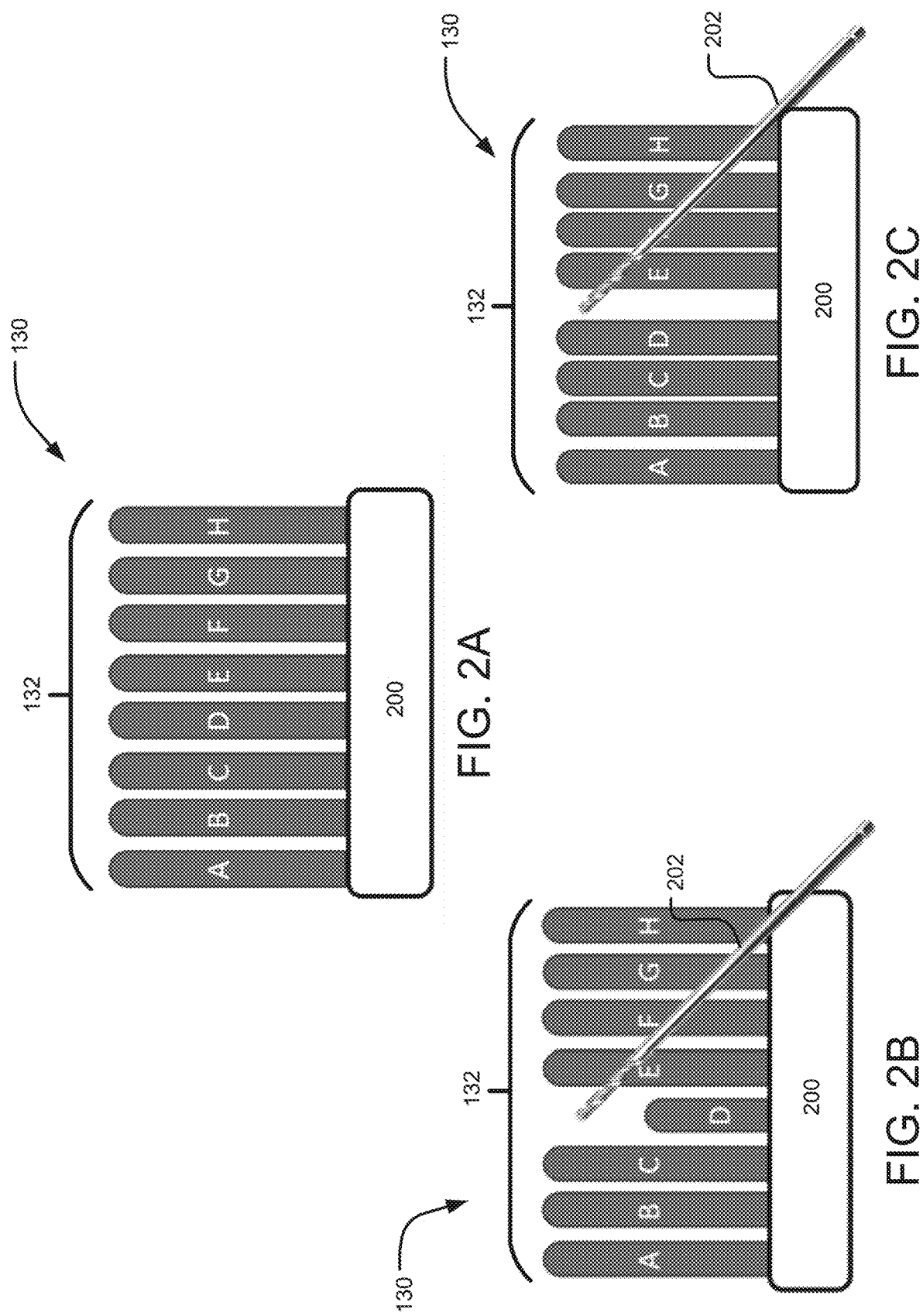
FIG. 2A is an image of a retractor according to at least one embodiment of the present disclosure.
FIG. 2B is an image of a retractor according to at least one embodiment of the present disclosure.
FIG. 2C is an image of a retractor according to at least one embodiment of the present disclosure.

FIGS. 2A, 2B, and 2C illustrate the retractor 130. In some embodiments, the retractor 130 may include a reference marker, as previously described. The reference marker may be tracked or detected by a navigation system 114 and/or may be depicted in at least one image (such that the at least one image may be used to determine a relative position or orientation of the retractor 130). In other embodiments, the retractor 130 includes a fluoroscopic marker detectable by a fluoroscope and useful during registration to identify the retractor 130 in a fluoroscopic image.

The retractor 130 includes elongate members 132 comprising elongate members 132A-H, as illustrated in FIG. 2A-2C. In some embodiments, the elongate members 132 include between three and ten elongate members. In other embodiments, the elongate members 132 include less than three elongate members or more than ten elongate members. In some embodiments, each of the elongate members 132 may have a length between 2-55 cm. In other embodiments, each of the elongate members 132 may have a length less than 2 cm or greater than 55 cm. In some embodiments, each of the elongate members 132 may have a width between 3-25 cm. In other embodiments, each of the elongate members 132 may have a length less than 3 cm or greater than 25 cm. Although depicted as having identical lengths in FIGS. 2A-2C, in some embodiments the elongate members 132 do not all have the same length. In some embodiments, each of the elongate members 132 may have a space between each adjacent elongate member spanning 1 cm. In other embodiments, each of the elongate members 132 may have a space between each adjacent elongate member 132 spanning less than 1 cm or greater than 1 cm. The elongate members 132 are configured to engage, retract, and hold patient soft tissue to expose an internal area of the patient for a surgical procedure.

In the illustrated embodiment, the elongate members 132 are attached to a base 200. The elongate members 132 may be movably and/or detachably attached to the base 200. In other embodiments, the elongate members 132 may be attached to any other component such as, for example, the robot 126. At least one elongate member 132 may include one segment in some embodiments. In other embodiments, at least one elongate member 132 may include multiple segments (e.g., may be articulated). In some embodiments, each elongate member 132 may include one segment or multiple segments. In other words, the elongate members 132 may all be articulated, may all be single-segmented, or may include a combination of single-segmented elongate members and articulated elongate members. The elongate members 132 may be made from any material including, but not limited to, metal, aluminum, stainless steel, or the like.

Each of the elongate members 132 is selectively movable. In embodiments where the elongate members 132 are articulated, each segment of each articulated elongate member 132 is selectively movable. In some embodiments, each elongate member 132 is independently movable from the other elongate members 132. In other embodiments, the elongate members 132 are movable together. When at least one of the elongate members 132 is identified to interfere with a trajectory of a surgical device 202, the identified elongate member 132 is operable to move away or to be moved away (whether with or without human input) from the surgical device 202. More than one elongate member 132 may be identified as interfering with a trajectory of the surgical device 202. Any identified elongate members 132 are movable without moving the entire retractor 130 (e.g., without removing or otherwise moving the base 200 and/or any remaining elongate members 132), thereby maintaining a position of the patient or of a portion of the patient's anatomy held in place by the retractor 130.

In some embodiments, as shown in FIG. 2B, where a surgical device 202 will impact an elongate member 132 (here, the elongate member 132 labeled D) of the retractor 130 when the surgical device 202 is moved along a predetermined trajectory, the elongate member 132D may be moved, or retracted, from an initial position, shown in FIG. 2A, toward the base 200 and away from the surgical device 202. In other embodiments, as shown in FIG. 2C, the elongate member 132 in question (here, again, the elongate member 132 labeled D) may be moved from the initial position shown in FIG. 2A toward an adjacent elongate member (here, 132C). In some instances, more than one elongate member, such as elongate members 132D and 132E, may move or be moved toward an adjacent elongate member 132 to free a path for the surgical device 202. In other embodiments, the identified elongate member 132 may be moved in any direction and/or to any orientation to avoid the surgical device 202. For example, in embodiments where the elongate members 132 are articulated or made of a selectively bendable material, the identified elongate member 132 may curl towards itself. In other embodiments, the elongate member 132 may be linearly and/or rotatably moved.

The one or more elongate members 132 may be moved automatically or manually. In some embodiments, a notification may be transmitted to a user that notifies the user to manually move the at least one elongate member 132. In such embodiments, the user may move the elongate member 132 without detaching the elongate member from the base 200, or the user may detach the elongate member 132 from the base 200, or the user may push a button, push or pull a lever, turn a crank, or otherwise operate a device that causes the elongate member 132 to move in a desired fashion. In other embodiments, the motor 134 is configured to selectively retract and extend (or otherwise move) at least one of the one or more elongate members 132. For example, in some embodiments, the motor 134 is configured to selectively retract at least one of the one or more elongate members 132 toward the base 200 upon receipt of a first signal from, for example, the processor 104. The motor 134 may also be configured to extend the at least one elongate member 132 from the base 200 upon receipt of a second signal (received after the first signal) from the processor 104. In some embodiments, more than one motor 134 may be used to move the one or more elongate members 132. For example, each elongate member 132 may be moved by a motor 134 dedicated to movement of that member, or each motor 134 of a plurality of motors 134 may move at least one elongate member 132.

Figure 3:
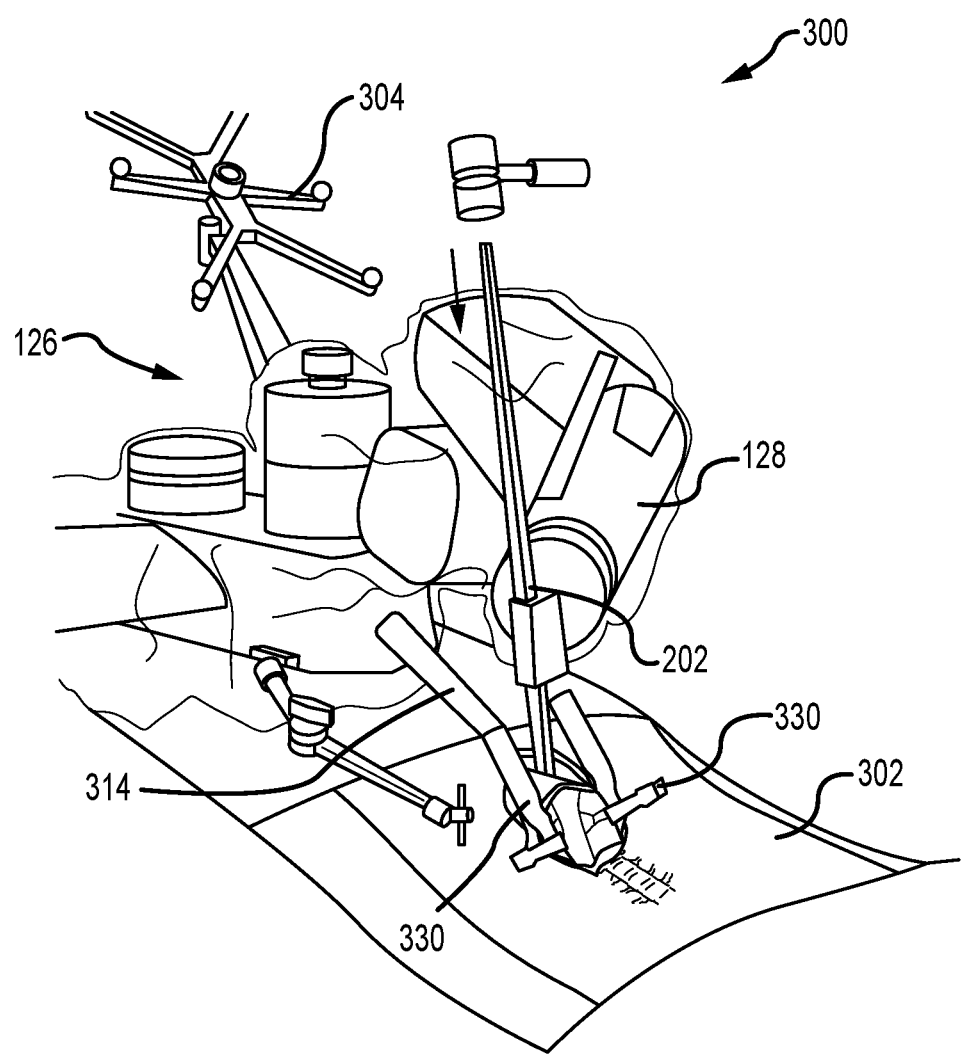
FIG. 3 is an image of a surgical robot fixedly secured to a retractor according to at least one embodiment of the present disclosure.

Turning to FIG. 3, at least a portion of an operating environment 300 is illustrated, including a robot 126 and a robot arm 128, a reference frame 304 disposed on the robot 126, a patient 302 laying prone, and two retractors 330. The retractors 330 illustrated in FIG. 3 are not the same as the retractors 130 illustrated in FIGS. 2A-2C and discussed above, but the retractors 130 could be used in the embodiment of FIG. 3. As illustrated, a surgical device 202 may be held by the robot arm 128. One retractor 330 is secured to (e.g., coupled to, connected to, affixed to, attached to, etc.)

the robot 126 with a rigid connector 314 to facilitate maintenance of a relative position of the robot 126 to the patient 302. The connector 314 may be a solid elongate member in some embodiments and may be an articulate member (selectively lockable in one or more positions) in other embodiments. The connector 314 may be made of radiolucent material or of a material that is not radiolucent. In some embodiments, the connector 314 may comprise one or more fluoroscopic markers, navigation markers, light-emitting diodes, geometric patterns, magnets, or other devices or objects useful for enabling a position and/or orientation of the connector 314 to be detected or sensed in an X-ray image, or by a navigation system (whether optical, electromagnetic, or otherwise), or by another sensor or system.

The connector 314 may be configured to be non-rigidly attached to a retractor 330 and to a robot 126 (for example, via ball-and-socket joints), so that the retractor 330 and the robot 126 can be moved relative to each other during initial positioning. Thereafter, the connector 314 may be lockable in place. In other words, once the retractor 330 and the robot 126 are properly positioned, the joints between the connector 314 on the one hand and the retractor 330 and robot 126 on the other hand may be locked, such that the connector 314 maintains the relative position of the retractor 330 to the robot 126.

Although FIG. 3 shows only one connector 314 securing only one retractor 330 to the robot 126, in some embodiments a connector 314 may be used to secure the second retractor 330 to the robot 126, and/or to secure any other retractor(s) 330 used during the surgical procedure to the robot 126. Also in some embodiments, a single connector 314 may be used to secure a plurality of retractors 330 to the robot 126. The connector 314 may, for example, be Y-shaped or otherwise comprise a fork such that a first end of the connector 314 may be connected to the robot 126 and a plurality of second ends of the connector 314 may be connected to one or more retractors 330.

In some embodiments, the connector 314 may be connected to the retractor 330 and the robot 126 only for a portion of a surgical procedure, while in other embodiments the connector 330 may remain connected to the retractor 330 and the robot 126 for the entire surgical procedure. Similarly, in some embodiments the connector 314 may be in a locked state (so as to maintain a fixed relative position of the robot 126 to the retractor 330) for only a portion of a surgical procedure, while in other embodiments the connector 314 may remain in a locked state for the entire surgical procedure. The connector 314 may be selectively lockable and unlockable.

Connecting the retractor 330 to the robot 126 may improve stability and restriction of movement of the patient 302, and adds an additional level of mechanical fixation of the patient 302. This is particularly beneficial after registration, given that registration—which is generally a time-intensive process—must be repeated if a patient 302 moves with respect to the robot 126 after the registration is complete.

Figure 4:
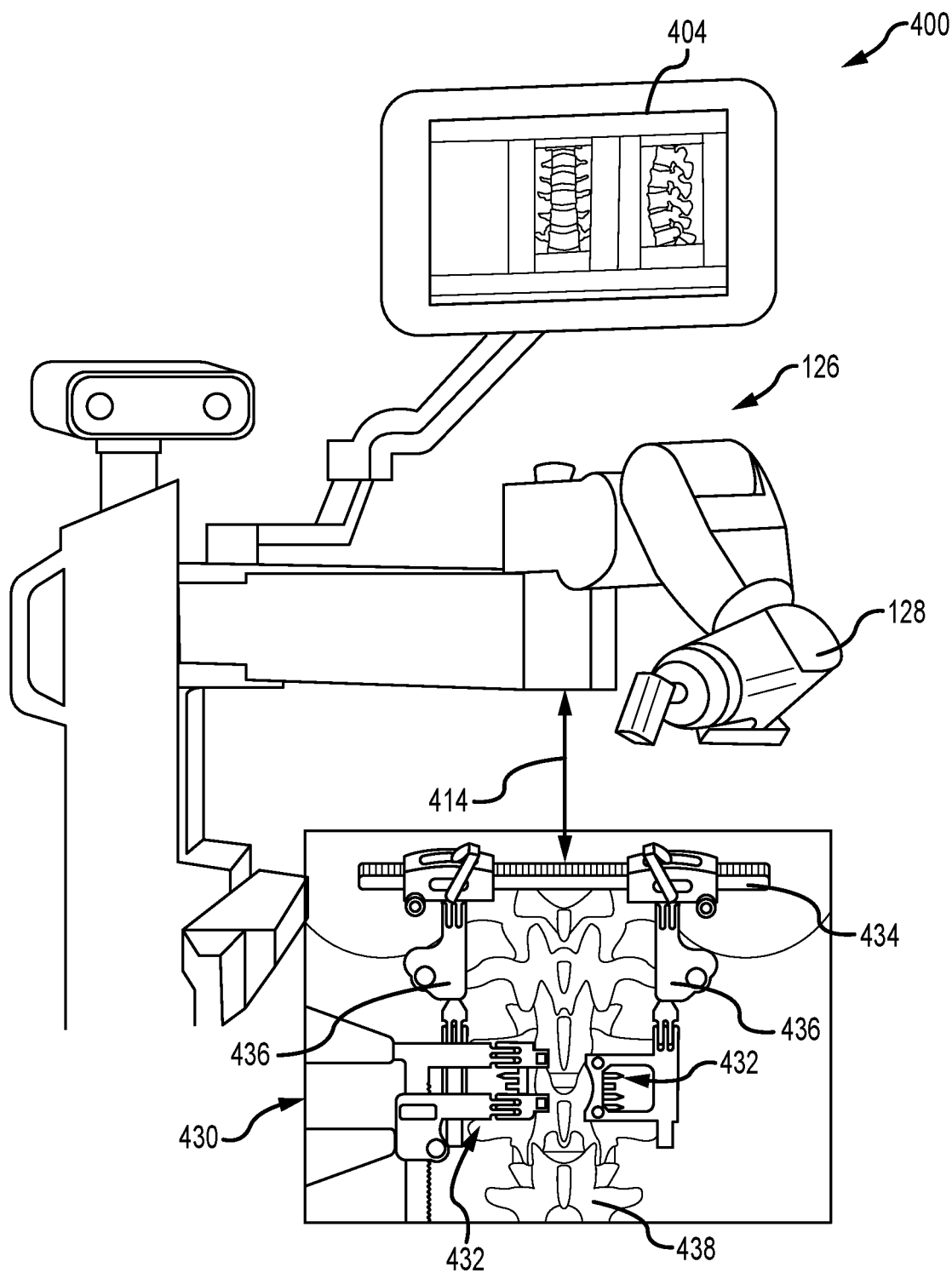
FIG. 4 is an image of a surgical robot fixedly secured to a retractor according to at least one embodiment of the present disclosure.

Turning to FIG. 4, at least a portion of another operating environment 400 is illustrated, including a robot 126 and a robot arm 128, a display 404, and a retractor 430. The retractor 430 as illustrated comprises a crossbar 434 to which two arms 436 are adjustably mounted. The arms 436 include one or more elongate members 432 for retracting a patient's soft tissue (not shown in FIG. 4) so as to gain access to the patient's spine 438.

A connector 414 (represented in FIG. 4 by an arrow) connects the retractor 430 to the robot 126. More specifically, the connector 414 is secured to the crossbar 434, and thus is secured via the crossbar 434 to the arms 436 and the elongate members 432. The elongate members 432 may be the same as or similar to the elongate members 132 described above.

The connector 414 may be the same as or similar to the connector 314 described above. For example, the connector 414 may be a solid elongate member in some embodiments and may be an articulate member in other embodiments. As described above, connecting the retractor 430 to the robot 126 may improve stability and restriction of movement of a patient, while adding an additional level of mechanical fixation of the patient (beyond, for example, any mechanical fixation of the robot to the patient provided by a direct connection between the robot and a bone of the patient). Further, the elongate members 432 of the retractor 430 are movable in some embodiments. As described above, this beneficially enables a path or trajectory for a tool to be cleared, if one or more of the elongate members 432 is positioned in or along the path or trajectory. In such embodiments, the combination of the connector 414 and the retractor 430 with the plurality of elongate members 432 provides additional stability to the patient while also allowing for unobstructed use of tools without removing or otherwise uninstalling the entire retractor 430.

Figure 5:
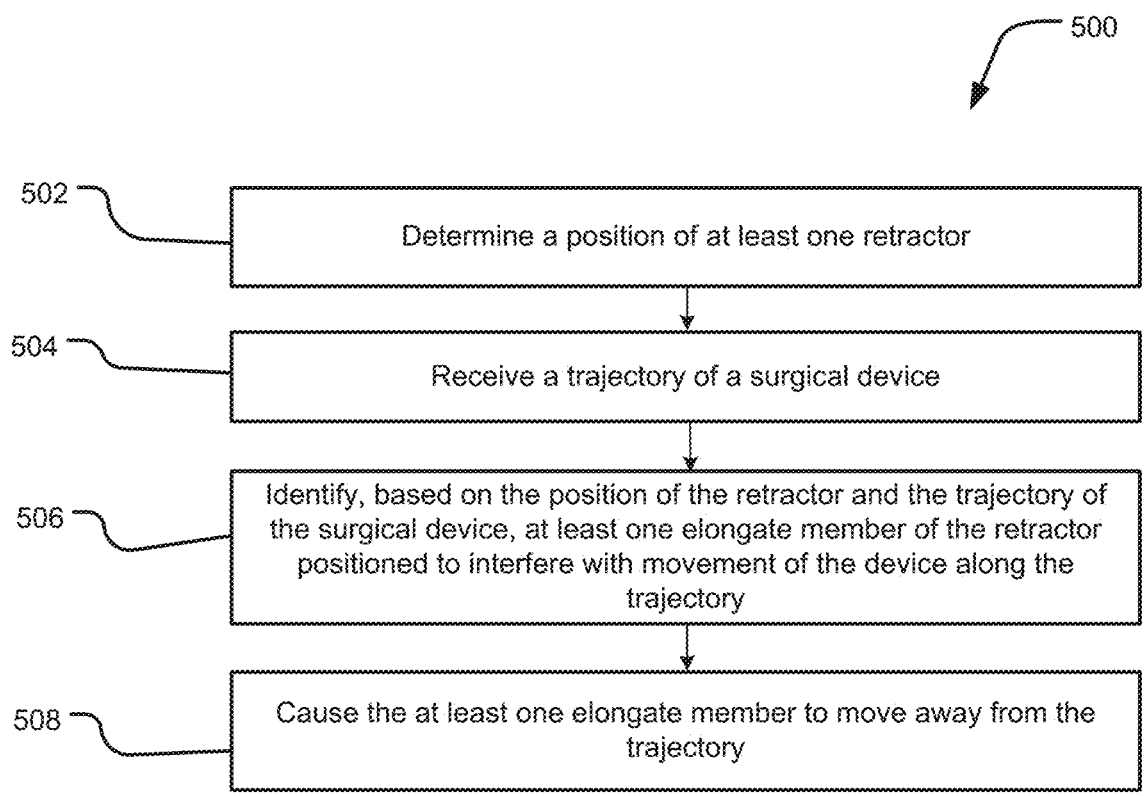
FIG. 5 is a flowchart of a method according to at least one embodiment of the present disclosure.

Turning now to FIG. 5, a method 500 for avoiding retractor interference may be executed, for example, in whole or in part, on a computing device such as the computing device 102 or a similar device, and more specifically on or by a processor such as the processor 104. Execution of the method 500 may require or utilize one or more other components of the system 100 or similar components. One or more aspects of the method 500 may be performed by or with a surgical robot such as the robot 126, a surgeon, or a combination of both using one or more imaging devices such as the imaging device 112.

The method 500 comprises determining a position of at least one retractor (step 502). The retractor may be, for example, the at least one retractor 130, 330, 430. The retractor may have a base, such as the base 200 or the arm 436, and one or more elongate members, such as the one or more elongate members 132, 432 extending from the base. The one or more elongate members may be moved manually or automatically (by, for example, the motor 134), and/or in any fashion described herein. In some embodiments, determining the position of the at least one retractor includes determining a position of each elongate member of the one or more elongate members.

The determining the position of the retractor may be based on images of the retractor taken with one or more imaging devices (e.g., the imaging device 112), navigation data from a navigation system (e.g., a navigation system 114), registration data, a surgical plan (e.g., a surgical plan 122), and/or sensor data from one or more sensors disposed on the retractor. For example, the retractors may comprise one or more encoders to facilitate determination of a position of each elongate member thereof relative to a base thereof. One or more image processing algorithms such as the image processing algorithm 116 may be utilized to identify the retractor in image data received from the imaging device. The image processing algorithm may also be used to determine a position of the retractor based on the images of the retractor. In other embodiments, the position of the retractor may be received through a user interface such as the user interface 110 from a surgeon or operator.

In other embodiments, the at least one retractor may be coupled to a robot (e.g., the robot 126), and determining the position of the at least one retractor may be based on robot positional data corresponding to a position of the robot. The robot positional data may include coordinates of and/or an orientation of the robot and/or a robotic arm such as the robotic arm 128. In some embodiments, the robot positional data may be received from a navigation system (e.g., the navigation system 114). In other embodiments, the robot positional data may be received from the robot. For example, the robot may include positional sensors for tracking and transmitting a position of the robot to, for example, the computing device. In other embodiments, the robot positional data may be received through the user interface from a surgeon or operator.

The method 500 also comprises receiving a trajectory of a surgical device (step 504). The trajectory may be received via the user interface and/or a communication interface such as the communication interface 108 of a computing device such as the computing device 102, and may be stored in a memory such as the memory 106. The trajectory may be sensed, determined, or calculated based on information about a movement of the surgical device, which information may be detected information, reported information, or other information. The trajectory may also be generated by or uploaded to any component of the system 100. The trajectory may also be part of a surgical plan such as the surgical plan 122 received via the user interface or the communication interface. The trajectory may include information about a surgical device such as the surgical device 202 (e.g., surgical device dimensions), a distance or length of the trajectory, and/or a duration for which the surgical device will remain positioned at an end of or elsewhere along the trajectory.

The method 500 also comprises identifying, based on the position of the retractor and the trajectory of the surgical device, at least one elongate member of the one or more elongate members positioned to interfere with movement of the device along the trajectory (step 506). An interference algorithm such as the interference algorithm 120 may be configured to identify the at least one elongate member positioned to interfere with movement of the device along the trajectory. In some embodiments, the interference may be determined by mapping the trajectory in a 3D model that includes the accurately positioned retractor and identifying any elongate members that interfere with the trajectory. In such embodiments, the surgeon may visibly identify the interference in the model, or the algorithm may identify the interference. In other embodiments, a surgeon or other operating room staff may simply identify an expected interference between the surgical device and one or more elongate members. The surgeon or other operating room staff may also utilize a user interface such as the user interface 110 to identify the one or more elongate members in question.

The method 500 also comprises causing the at least one elongate member to move from an initial position and away from the trajectory (step 508). The movement may happen automatically (without human input) or manually. As described with respect to FIGS. 2B and 2C, the at least one elongate member may be moved, or retracted, towards the base and away from the surgical device. For example, the at least one elongate member may be bent upward or downward or to one side or another, or curled upward or downward or to one side or another. In some embodiments, the at least one elongate member may be slid or otherwise moved towards an adjacent elongate member and in some instances, more than one elongate member may slide or otherwise move (or be slid or otherwise moved) towards an adjacent elongate member to form a clear path for the surgical device. In other embodiments, the at least one elongate member may be moved in any direction and moved to any orientation to avoid the surgical device. For example, in embodiments where the at least one elongate member is articulated, the at least one elongate member may curl towards itself. In other embodiments, the at least one elongate member may be linearly and/or rotatably moved. Also in some embodiments, the at least one elongate member may be detached or otherwise disconnected from the base, whether automatically or manually.

The method 500 may also comprise transmitting a notification for notifying a user to manually move the at least one elongate member. The notification may be displayed on a display of a user interface and may be visually and/or audibly communicated to the user. The notification may include instructions, such as retractor instructions 124, for the user to move the at least one elongate member away from the trajectory and/or for the user to move the at least one elongate member towards the trajectory.

The method 500 may comprise receiving a surgical plan, which may be the same as or similar to the surgical plan 122. The surgical plan may be received via the user interface and/or the communication interface, and may be stored in the memory. The surgical plan may include information about one or more planned movements (e.g., one or more trajectories) of the surgical device held by a robotic arm such as the robotic arm 128 during a surgical procedure. The information may also include a timeline or schedule of the one or more planned movements. The one or more planned movements may include one or more of timestamps, a type of movement (e.g., translational and/or rotational), a duration of the movement, and/or positional information (e.g., coordinates and/or orientation).

In some embodiments, the method 500 may comprise determining information about one or more needed movements (including, for example, one or more trajectories) of the tool during a surgical procedure outlined or otherwise described in a surgical plan. In such embodiments, the surgical plan may not include receiving any such information via a computing device, but a processor, executing instructions stored in a memory, may generate such information based on the surgical plan.

Figure 6:
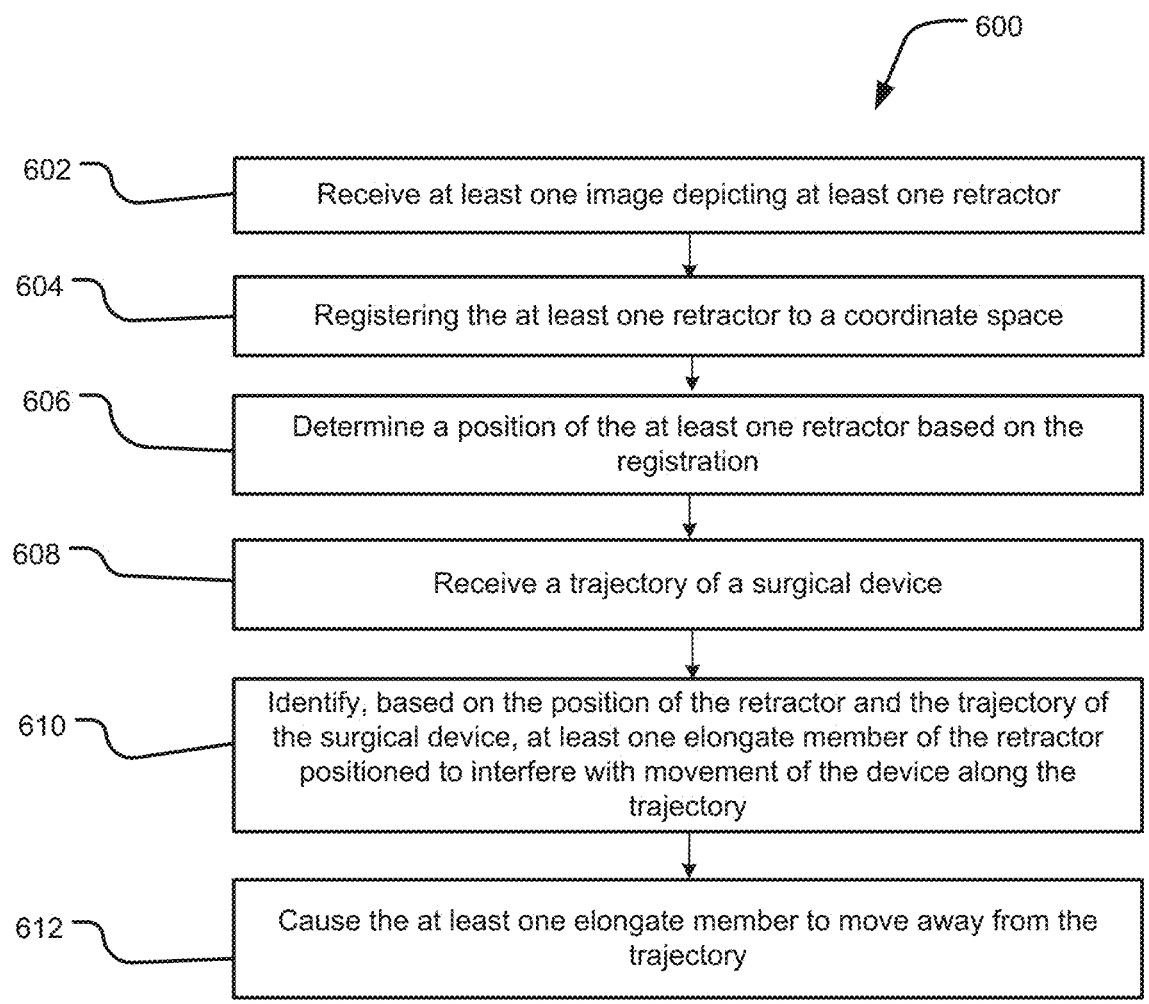
FIG. 6 is another flowchart of a method according to at least one embodiment of the present disclosure.

Turning now to FIG. 6, a method 600 for avoiding retractor interference may be executed, for example, in whole or in part, on a computing device such as the computing device 102 or similar device, and more specifically on or by a processor such as the processor 104. Execution of the method 600 may require or utilize one or more other components of the system 100 or similar components. One or more aspects of the method 600 may be performed by or with a surgical robot such as the robot 126, a surgeon, or a combination of both using one or more imaging devices such as the imaging device 112.

The method 600 comprises receiving at least one image depicting at least one retractor, such as the retractor 130, 330, 430 (step 602). In embodiments where the at least one retractor includes a reference frame, the at least one image may also depict the reference frame. In some embodiments, the at least one image is a single image. In other embodiments, the at least one image includes more than one image. The at least one image may be one or more two-dimensional (2D) images, one or more three-dimensional (3D) images, or a combination of 2D and 3D images. In some embodiments, the at least one image is a 3D model of the at least one retractor. The at least one image may be received via a user interface such as the user interface 110 and/or a communication interface such as the communication interface 108 of a computing device such as the computing device 102, and may be stored in a memory such as the memory 106. The at least one image may also be generated by or uploaded to any component of the system 100. In some embodiments, the at least one image may be generated by an imaging device such as the imaging device 112, and may be received directly from the imaging device, or indirectly via any other component of the system 100 or a node of a network to which the system 100 is connected. In such embodiments, the at least one image may be received via, for example, the communication interface.

The at least one image may depict the at least one retractor and an anatomical element of a patient. The at least one image may be processed using an image processing algorithm such as the imaging processing algorithm 116 to identify the anatomical element and the at least one retractor in the image. In some embodiments, feature recognition may be used to identify a feature of the anatomical element and/or the retractor. For example, a contour of a vertebrae may be identified in the image, or a specific contour of the retractor may be identified. In some embodiments, the retractor may comprise one or more light-emitting diodes, geometric patterns, or other optical markers to facilitate identification thereof in the image. In other embodiments, the image processing algorithm may use artificial intelligence or machine learning to identify the anatomical element and/or the retractor.

The method 600 also comprises registering the at least one retractor to a coordinate space (step 604). The coordinate space may be a robot coordinate space, a patient coordinate space, or any other 3D coordinate space. A registration algorithm such as the registration algorithm 118 may be configured to locate the at least one retractor, the anatomical element, and/or the robot in the 3D coordinate space. In some embodiments, the algorithm may be configured to locate the at least one retractor in the 3D coordinate space by relating a known position of the robot (in embodiments where the at least one retractor is connected to the robot, e.g., with a connector 314 or 414) to a position of the patient based on the at least one retractor and the anatomical element depicted in the at least one image. In other words, the algorithm may determine a positional relationship between a position of the robot and the anatomical element based on a detected position of the retractor relative to the anatomical element, and a known position of the robot relative to the retractor.

The method 600 comprises determining a position of at least one retractor based on the registration (step 606). The retractor may have a base, such as the base 200 or the arm 436 and one or more elongate members, such as the one or more elongate members 132, 432 extending from the base. The one or more elongate members may be moved manually or automatically (by, for example, the motor 134) and/or in any other manner described herein. In some embodiments, determining the position of the at least one retractor includes determining a position of each elongate member of the one or more elongate members based on the registration.

The determining the position of the retractor may be based on images of the retractor taken with one or more imaging devices (e.g., the imaging device 112), navigation data from a navigation system (e.g., the navigation system 114), registration data, a surgical plan (e.g., a surgical plan 122), sensor data from one or more sensors disposed on the retractor, etc. For example, the retractors may comprise one or more encoders to facilitate determination of a position of each elongate member thereof relative to a base thereof. One or more image processing algorithms such as the image processing algorithm 116 may be utilized to identify the retractor in image data received from the imaging device. The image processing algorithm may also be used to determine a position of the retractor based on the images of the retractor. In other embodiments, the position of the retractor may be received through the user interface from a surgeon or operator.

In other embodiments, the at least one retractor may be coupled to a robot (e.g., via a connector 314 or 414), such as the robot 126, and determining the position of the at least one retractor may be based on robot positional data corresponding to a position of the robot. The robot positional data may include coordinates of and/or an orientation of the robot and/or a robotic arm such as the robotic arm 128. In some embodiments, the robot positional data may be received from a navigation system such as the navigation system 114. In other embodiments, the robot positional data may be received from the robot. For example, the robot may include positional sensors for tracking and transmitting a position of the robot to, for example, the computing device. In other embodiments, the robot positional data may be received through the user interface 110 from a surgeon or operator.

One or more aspects of the determining a position of at least one retractor in the step 606 may be the same as or similar to one or more aspects of determining a position of the at least one retractor in the step 502.

The method 600 also comprises receiving a trajectory of a surgical device (step 608). The receiving may be the same as or similar to the receiving a trajectory of a surgical device as described above in connection with the step 504. The trajectory may be received via the user interface and/or a communication interface such as the communication interface 108 of a computing device such as the computing device 102, and may be stored in a memory such as the memory 106. The trajectory may be sensed, determined, or calculated based on information about a movement of the surgical device, which information may be detected information, reported information, or other information. The trajectory may also be generated by or uploaded to any component of the system 100. The trajectory may also be part of a surgical plan such as the surgical plan 122 received via the user interface or the communication interface. The trajectory may include information about a surgical device such as the surgical device 202 (e.g., surgical device dimensions), a distance or length of the trajectory, and/or a duration for which the surgical device will remain positioned at an end of or elsewhere along the trajectory.

The method 600 also comprises identifying, based on the position of the retractor and the trajectory of the surgical device, at least one elongate member of the one or more elongate members positioned to interfere with movement of the device along the trajectory (step 610). An interference algorithm such as the interference algorithm 120 may be configured to identify the at least one elongate member positioned to interfere with movement of the device along the trajectory. In some embodiments, the interference may be determined by mapping the trajectory in a 3D model that includes the accurately positioned retractor and identifying any elongate members that interfere with the trajectory. In such embodiments, the surgeon may visibly identify the interference in the model, or the algorithm may identify the interference. In other embodiments, a surgeon or other operating room staff may simply identify an expected interference between the surgical device and one or more elongate members. The surgeon or other operating room staff may also utilize a user interface such as the user interface 110 to identify the one or more elongate members in question.

One or more aspects of the identifying at least one elongate member of the one or more elongate members positioned to interfere with movement of the device along the trajectory in the step 610 may be the same as or similar to one or more aspects of identifying at least one elongate member of the one or more elongate members positioned to interfere with movement of the device along the trajectory in the step 506.

The method 600 also comprises causing the at least one elongate member to move away from the trajectory (step 612). When the at least one elongate member moves away from the trajectory, the at least one elongate member also moves from an initial position. The movement may happen automatically (without human input) or manually. As described with respect to FIGS. 2B and 2C, the at least one elongate member may be moved, or retracted, towards the base and away from the surgical device. For example, the at least one elongate member may be bent upward or downward or to one side or another, or curled upward or downward or to one side or another. In some embodiments, the at least one elongate member may be slid or otherwise moved towards an adjacent elongate member and in some instances, more than one elongate member may slide or otherwise move (or be slid or otherwise moved) towards an adjacent elongate member to form a clear path for the surgical device. In other embodiments, the at least one elongate member may be moved in any direction and moved to any orientation to avoid the surgical device. For example, in embodiments where the at least one elongate member is articulated, the at least one elongate member may curl towards itself. In other embodiments, the at least one elongate member may be linearly and/or rotatably moved. Also in some embodiments, the at least one elongate member may be detached or otherwise disconnected from the base, whether automatically or manually.

One or more aspects of the causing the at least one elongate member to move from an initial position and away from the trajectory in the step 612 may be the same as or similar to one or more aspects of causing the at least one elongate member to move from an initial position and away from the trajectory in the step 508.

The method 600 may also comprise transmitting a notification for notifying a user to manually move the at least one elongate member. The notification may be displayed on a display of a user interface and may be visually and/or audibly communicated to the user. The notification may include instructions, such as retractor instructions 124, for the user to move the at least one elongate member away from the trajectory and/or for the user to move the at least one elongate member towards the trajectory.

The method 600 may comprise receiving a surgical plan, which may be the same as or similar to the surgical plan 122. The surgical plan may be received via the user interface and/or the communication interface, and may be stored in the memory. The surgical plan may include information about one or more planned movements (e.g., one or more trajectories) of the surgical device held by a robotic arm such as the robotic arm 128 during a surgical procedure. The information may also include a timeline or schedule of the one or more planned movements. The one or more planned movements may include one or more of timestamps, a type of movement (e.g., translational and/or rotational), a duration of the movement, and/or positional information (e.g., coordinates and/or orientation).

In some embodiments, the method 600 may comprise determining information about one or more needed movements (including, for example, one or more trajectories) of the tool during a surgical procedure outlined or otherwise described in a surgical plan. In such embodiments, the surgical plan may not include receiving any such information via a computing device, but a processor, executing instructions stored in a memory, may generate such information based on the surgical plan.

The methods and systems described herein provide a retractor having one or more elongate members capable of being moved or removed or of moving to avoid interference with a surgical device. The movement or removal of the elongate members without removing or otherwise uninstalling the retractor reduces operating time as the retractor does not need to be continuously reinstalled and uninstalled, and helps to avoid having to repeat a registration process. The retractor may also be connected directly to a robot, thereby providing additional stability and rigidity to a patient (and further reducing a chance of needing to repeat a registration process). Thus, methods and systems for avoiding retractor interference with a surgical device provide for a streamlined process to retract or otherwise move elongate members of the retractor to avoid interference with the surgical device without disturbance to the surgical site or retracted area.

As may be appreciated based on the foregoing disclosure, the present disclosure encompasses methods with fewer than all of the steps identified in FIGS. 5 and 6 (and the corresponding description of the methods 500 and 600), as well as methods that include additional steps beyond those identified in FIGS. 5 and 6 (and the corresponding description of the methods 500 and 600). Methods of the present disclosure explicitly include methods with one or more steps described above as part of the method 500 and one or more steps described above as part of the method 600.

The foregoing discussion has been presented for purposes of illustration and description. The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system for retractor interference avoidance comprising:
   at least one retractor having a base and two or more elongate members extending from the base, the two or more elongate members being movable;
   a memory for storing instructions; and
   a processor executing instructions stored in the memory that cause the processor to:
   determine a position of the at least one retractor;
   receive a trajectory of a surgical device;
   identify, based on the position of the at least one retractor and the trajectory of the surgical device, at least one elongate member of the two or more elongate members in an initial position that obstructs movement of the surgical device along the trajectory; and
   cause the at least one elongate member to move out of the initial position while at least one of the base and a second elongate member remains fixed so that the movement of the surgical device is no longer obstructed.

2. The system of claim 1, further comprising at least one motor for moving the at least one elongate member.

3. The system of claim 1, wherein executing the instructions stored in the memory further causes the processor to transmit a notification for notifying a user to manually move the at least one elongate member.

4. The system of claim 1, wherein executing the instructions stored in the memory further causes the processor to receive robot positional data corresponding to a position of a robot, the at least one retractor coupled to the robot.

5. The system of claim 4, wherein determining the position of the at least one retractor is based on the robot positional data.

6. The system of claim 1, wherein executing the instructions stored in the memory further causes the processor to:
   receive at least one image depicting the at least one retractor; and
   register the at least one retractor to a patient space, wherein determining the position of the at least one retractor is based on the registration.

7. The system of claim 6, wherein executing the instructions stored in the memory further causes the processor to receive a three-dimensional (3D) model of the at least one retractor, and wherein the registration is further based on the 3D model.

8. The system of claim 1, wherein the at least one retractor includes a fluoroscopic marker detectable by a fluoroscope.

9. The system of claim 1, wherein executing the instructions stored in the memory further causes the processor to cause the at least one elongate member to return to the initial position.

10. The system of claim 1, wherein the at least one retractor comprises two elongate members adjustably mounted to a crossbar, and wherein the two elongate members are configured to retract soft tissue of a patient.

* * * * *